United States Patent [19]
Sezginer et al.

[11] Patent Number: 6,166,543
[45] Date of Patent: Dec. 26, 2000

[54] METHOD AND APPARATUS FOR MEASURING NUCLEAR MAGNETIC RESONANCE

[75] Inventors: Abdurrahman Sezginer, Houston, Tex.; Pabitra N. Sen, Ridgefield, Conn.; Mohammad Reza Taherian, Stafford; Boqin Sun, Sugar Land, both of Tex.

[73] Assignee: Schlumberger Technology Corporation, Houston, Tex.

[21] Appl. No.: 08/936,892

[22] Filed: Sep. 25, 1997

[51] Int. Cl.$^7$ .................................................. G01U 3/00
[52] U.S. Cl. ............................................................ 324/303
[58] Field of Search ..................................... 324/300–322

[56] References Cited

U.S. PATENT DOCUMENTS

| | | |
|---|---|---|
| 4,035,718 | 7/1977 | Chandler . |
| 4,443,760 | 4/1984 | Edelstein et al. ........................ 324/309 |
| 4,528,508 | 7/1985 | Vail, III . |
| 4,656,422 | 4/1987 | Vail, III et al. . |

(List continued on next page.)

FOREIGN PATENT DOCUMENTS

| | | |
|---|---|---|
| PCT/EP96/ 02691 | 6/1996 | WIPO . |
| PCT/US96/ 15301 | 9/1996 | WIPO . |

OTHER PUBLICATIONS

Bushberg textbook The Essential Physics of Medical Imaging ISBN#0–683–01140–5 copyright 1994 pp. 127–131, 317–325, and 328–330 No month year only.

Bushong textbook Magnetic Resonance Imaging Physical and Biological Principles ISBN#0–8151–1342–0 copyright 1996 chapter 3 pp. 48–49, chapter 8 pp. 95–98, Glossary pp. 476 and 482. No month year only.

D.V. Trushkin, O.A. Shushakov, & A.V. Legchenko, "Surface NMR Applied to an Electroconductive Medium", Geophysical Prospecting, 1995, 43, 623–633.

O.A. Shushakov, "Surface NMR Measurement of Proton Relaxation Times in Medium to Coarse–Grained Sand Aquifer", 1996, Magnetic Resonance Imaging, vol. 14, Nos. 7/8, pp. 959–960.

R.C. Herrick, S.H. Couturie, & D.L. Best, "An Improved Nuclear Magnetism Logging System and Its Application to Formation Evaluation", Sep. 23–26, 1979, Las Vegas, Nevada, SPE8361.

S. C. Bushong, ScD, "Magnetic Resonance Imaging Physical and Biological Principles", Houston, Texas, pp. 279–297.

Bagguley, D.M.S., "Pulsed Magnetic Resoance: NMR, ESR, and Optics A recognition of E. L. Hahn", 1992, pp. 317–345.

Primary Examiner—Christine K. Oda
Assistant Examiner—Tiffany A. Fetzner
Attorney, Agent, or Firm—John J. Ryberg; Brigitte L. Jeffery

[57] ABSTRACT

The present invention relates generally to an apparatus and method for measuring nuclear magnetic resonance properties of an earth formation traversed by a borehole by generating gradient-echoes. The measurement can be made while drilling or using a wireline tool. The apparatus applies a static magnetic field, $B_a$, in a volume of the formation which polarizes the nuclei of hydrogenous connate fluids within the formation. The apparatus applies a second magnetic field, $B_b$, in a volume of the formation. The magnetic fields $B_a$ and $B_b$ are substantially orthogonal in the volume of the formation. A change in the polarity of the magnetic field, $B_b$, reverses the direction of precession of the nuclei thereby generating a train of gradient-echoes. Each gradient-echo signal is transformed into the frequency domain and the signal frequency is mapped to a radial position in the volume of the formation in order to generate an image of the formation. Various properties of the formation, such as the effective diffusion coefficient of the formation fluid, longitudinal relaxation time, spin—spin relaxation time, and porosity can be estimated from the train of gradient-echoes.

63 Claims, 5 Drawing Sheets

U.S. PATENT DOCUMENTS

| | | |
|---|---|---|
| 4,717,878 | 1/1988 | Taicher et al. . |
| 4,724,385 | 2/1988 | Vail, III . |
| 4,804,918 | 2/1989 | Vail, III . |
| 4,808,928 | 2/1989 | Frahm et al. ............................ 324/309 |
| 4,933,638 | 6/1990 | Kenyon et al. ......................... 324/303 |
| 5,055,787 | 10/1991 | Kleinberg et al. . |
| 5,270,654 | 12/1993 | Feinberg et al. ........................ 324/309 |
| 5,363,041 | 11/1994 | Sezginer . |
| 5,428,291 | 6/1995 | Thomann et al. . |
| 5,596,274 | 1/1997 | Sezginer . |
| 5,629,624 | 5/1997 | Carlson et al. ......................... 324/309 |

METHOD AND APPARATUS FOR MEASURING NUCLEAR MAGNETIC RESONANCE

BACKGROUND OF THE INVENTION

The present invention relates generally to an apparatus and method for measuring nuclear magnetic resonance properties of an earth formation traversed by a borehole, and more particularly, to an apparatus and method for increasing the lateral measurement of nuclear magnetic resonance properties of an earth formation.

It is well recognized that most of the particles of an earth formation having non-zero nuclear spin magnetic moment, for example protons, have a tendency to align with a static magnetic field imposed on the formation. Such a magnetic field may be naturally generated, as is the case for the earth's magnetic field, $B_E$. After an RF pulse is supplied by a second oscillating magnetic field $B_1$, transverse to $B_E$, the protons will tend to precess about the $B_E$ vector with a characteristic resonance or Larmor frequency $\omega_L$ which depends on the strength of the static magnetic field and the gyromagnetic ratio of the particle. Hydrogen nuclei (protons) precessing about a magnetic field $B_E$ of 0.5 gauss, for example, have a characteristic frequency of approximately 2 kHz. If a population of hydrogen nuclei were made to precess in phase, the combined magnetic fields of the protons can generate a detectable oscillating voltage, known to those skilled in the art as a spin echo, in a receiver coil. Hydrogen nuclei of water and hydrocarbons occurring in rock pores produce NMR signals distinct from signals arising from other solids.

The NML™ nuclear magnetic logging tool of Schlumberger measures the free precession of proton nuclear magnetic moments in the earth's magnetic field. See U.S. Pat. No. 4,035,718 issued to Richard N. Chandler. The tool has at least one multi-turn coil wound on a core of non-magnetic material. The coil is coupled to the electronic circuitry of the tool and cooperatively arranged for periodically applying a strong DC polarizing magnetic field, $B_p$, to the formation in order to align proton spins approximately perpendicular to the earth's field, $B_E$. The characteristic time constant for the exponential buildup of this spin polarization is called the spin-lattice relaxation time, $T_1$. At the end of polarization, the field is rapidly terminated. Since the spins are unable to follow this sudden change, they are left aligned perpendicular to $B_E$ and therefore precess about the earth's field at the Larmor frequency $f_L = \gamma B_E$, where $\gamma$ is the gyromagnetic ratio of the proton. The Larmor frequency in the earth's field varies from approximately 1300 to 2600 Hz, depending on location. The spin precession induces in the coil a sinusoidal signal of frequency $f_L$ whose amplitude is proportional to the number of protons present in the formation. Additives in the borehole fluid are required to prevent the borehole fluid signal from obscuring the formation signal. The tool determines the amount of free fluid in the formation, the remainder of the pore space assumed to be occupied by bound fluid.

A further nuclear magnetic resonance approach employs a locally generated static magnetic field, $B_o$, which may be produced by one or more permanent magnets, and RF antennas to excite and detect nuclear magnetic resonance to determine porosity, free fluid ratio, and permeability of a formation. See U.S. Pat. No. 4,717,878 issued to Taicher et al. and U.S. Pat. No. 5,055,787 issued to Kleinberg et al. Nuclear spins align with the applied field $B_o$ with a time constant of $T_1$ generating a nuclear magnetic moment. The angle between the nuclear magnetization and the applied field can be changed by applying an RF field, $B_1$, perpendicular to the static field $B_o$. The frequency of the RF field must be the Larmor frequency. After application of an RF pulse, the protons begin to precess in the plane perpendicular to $B_0$ and generate a sequence of spin-echoes which produce a detectable signal in the antenna.

Nuclear magnetic resonance has proven useful in medical applications to perform noninvasive examinations of the interior organs and structures of an organism. See P. Mansfield, Pulsed Magnetic Resonance: NMR, ESR, and Optics, 317–345 (D. M. S. Baugguley ed., Cleardon Press, Oxford, 1992). The desire for faster imaging led to the development of commercial and laboratory NMR imaging systems in the medical field which use various gradient-echo techniques consisting of radiofrequency pulses, $\alpha$, in combination with switched magnetic field gradients to generate an image. See Stewart C. Bushong, Magnetic Resonance Imaging: Physical and Biological Principles, 279–286, (2d edition 1996). Known techniques such as fast low angle shot (FLASH) and fast imaging with steady state precession (FISP) require an RF excitation pulse, $\alpha$, of approximately 90° while other techniques vary the flip angle between 30° and 70° to maximize magnetic resonance strength.

While the tools and techniques developed in the prior art extract information about fluid properties, the tools and techniques have a disadvantage which limit their utility in practical applications. With a nuclear magnetic logging tool, as explained in U.S. Pat. No. 4,717,877 issued to Taicher et al., shell regions of differing radial separations from the longitudinal axis may be subjected to nuclear magnetic resonance excitation by varying the RF field frequency. Due to the required application of the RF field, the precession frequency is fixed, and the measurement, lateral from the borehole axis, of nuclear magnetic resonance properties of an earth formation is constrained to a thin shell region which provides a shallow depth of investigation relatively close to the borehole wall. Therefore, there is a need for a nuclear magnetic resonance system and method for determining a characteristic of an earth formation which does not require the use of an RF pulse to generate spin echoes.

SUMMARY OF THE INVENTION

The above disadvantages of the prior art are overcome by means of the subject invention for an apparatus and method for measuring nuclear magnetic resonance properties of an earth formation traversed by a borehole by generating gradient-echoes. The measurement can be made while drilling or using a wireline tool. The apparatus comprises a means for applying a static magnetic field, $B_a$, in a volume of the formation which polarizes the nuclei of hydrogenous connate fluids within the formation, and a means for applying a magnetic field, $B_b$, in a volume of the formation. Preferably, the magnetic fields $B_a$ and $B_b$ are substantially orthogonal in the volume of the formation. A change in the polarity of the magnetic field, $B_b$, reverses the direction of precession of the nuclei thereby generating a gradient-echo. The apparatus further comprises a means for detecting a signal induced in the formation after the nuclei begin to precess in the plane perpendicular to $B_b$. The apparatus further comprises means for transforming the gradient-echo signal into the frequency domain and means for mapping the signal frequency to a radial position in the volume of the formation.

The means for applying the static magnetic field, $B_a$, comprises a first coil wound on a magnetic body and a current source which supplies direct current to the first coil. The means for applying the magnetic field, $B_b$, comprises a second coil wound on a magnetic body and a current source which supplies an alternating current signal to the second coil. To generate the gradient-echoes, the first coil is selected and activated for a time period approximately equal to the longitudinal relaxation time of the formation. Following the time period, the first coil is deactivated and the second coil is selected and activated after the current ceases to flow through the first coil. A resonator sustains the current in the first or second coil during selective activation of the first or second coil. The gradient-echoes are detected by the first coil and a value representing a characteristic of the earth formation is derived from the gradient-echoes and transmitted to the surface or stored downhole.

The method of the subject invention comprises the steps of applying a static magnetic field, $B_a$, in a volume of the formation which polarizes the nuclei of hydrogenous connate fluids within the formation, and applying a magnetic field, $B_b$, in a volume of the formation. Preferably, the magnetic fields $B_a$ and $B_b$ are substantially orthogonal in the volume of the formation. A change in the polarity of the magnetic field, $B_b$, reverses the direction of precession of the nuclei thereby generating a gradient-echo. The method further comprises the steps of detecting a signal induced in the formation after the nuclei begin to precess in the plane perpendicular to $B_b$ and transforming the gradient-echo signal into the frequency domain. The signal frequency is mapped to a radial position in the volume of the formation.

BRIEF DESCRIPTION OF THE DRAWINGS

The advantages of the present invention will become apparent from the following description of the accompanying drawings. It is to be understood that the drawings are to be used for the purpose of illustration only, and not as a definition of the invention.

In the drawings.

DETAILED DESCRIPTION OF THE PREFERRED EMBODIMENT

Figure 1:
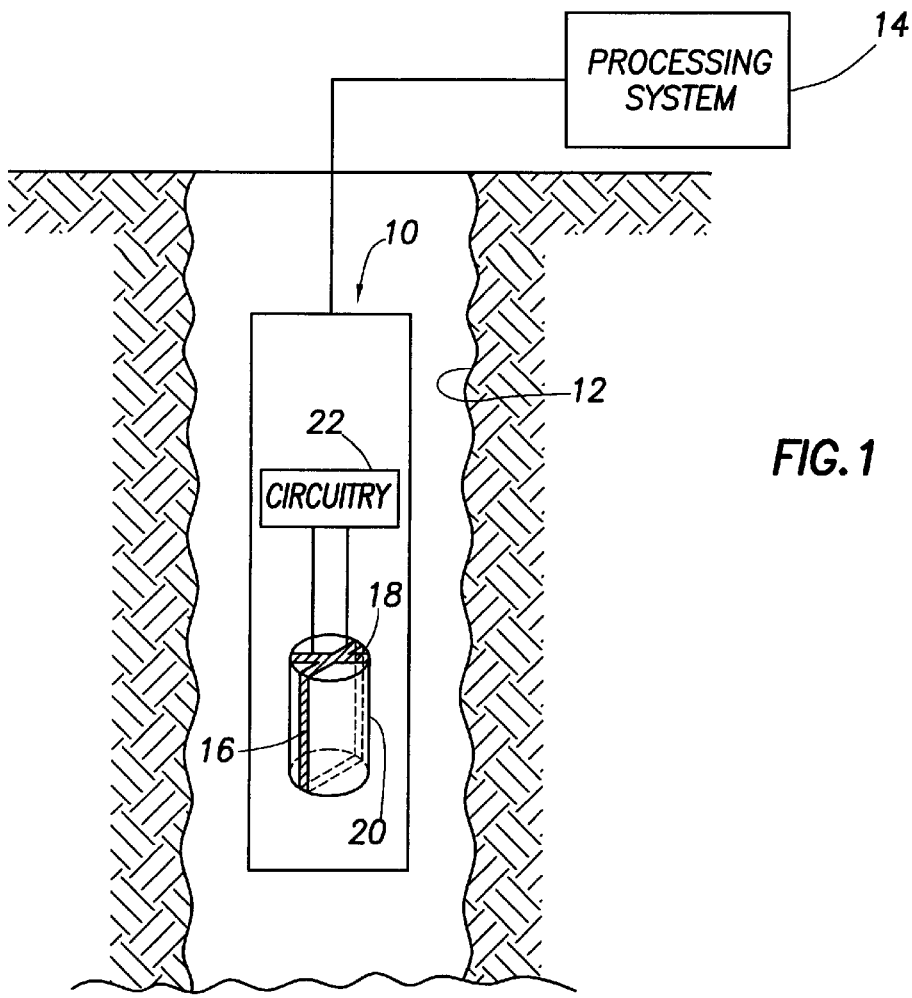
FIG. 1 illustrates a nuclear magnetic resonance (NMR) logging system.

Referring to FIG. 1, a nuclear magnetic resonance (NMR) logging system is illustrated. The NMR logging system includes a logging tool 10 disposed in a borehole 12 and connected via a wireline to a processing system 14 disposed at the borehole surface for processing signals transmitted uphole by the logging tool 10. Alternatively, the processing system 14 may be located downhole. The tool 10 has a pair of orthogonal coils 16, 18 wound on a non-conductive core 20. In a preferred embodiment, a non-conductive, magnetically permeable core 20 is made of a suitable material such as ferrite, laminated permealloy, or tape-wound metglass. However, a non-conductive, non-magnetically permeable core 20 is within contemplation of this invention. The inhomogeneous magnetic fields $B_a$ and $B_b$ arising from the coils 16, 18 are substantially orthogonal in the formation. The earth's field, $B_E$, is negligible compared to both $B_a$ and $B_b$. In a preferred embodiment, the coils 16, 18 are wound longitudinally around the core 20. The angular density of the windings is sinusoidal to insure a two-dimensional dipolar field distribution. The coils 16, 18 are azimuthally offset by 90° to insure the dipolar fields of the coils 16, 18 are orthogonal in the formation and the mutual inductance of the coils 16, 18 is minimal. In an alternate embodiment, one coil 16 is wound longitudinally around the core 20 and the other coil 18 is wound circumferentially around the core 20. The coils 16, 18 are coupled to the electronic circuitry 22 of the tool 10.

Figure 2:
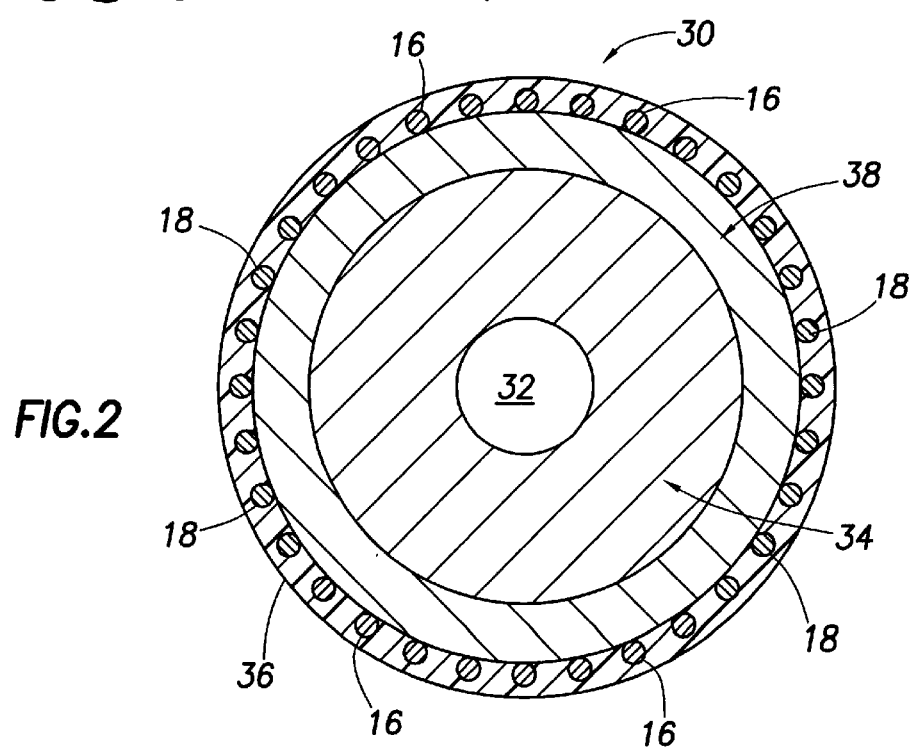
FIG. 2 illustrates a cross section of an NMR logging-while-drilling tool.

The present invention is useful in a logging-while drilling application. FIG. 2 illustrates a cross section of an NMR logging-while-drilling tool 30. The tool 30 includes a mud channel 32 for carrying the borehole fluid through the drill string and a drill collar 34, the external member of the tool 30 that is in contact with the drilling fluid and rock cuttings in the borehole and the earth formation in which the well is drilled. The coils 16, 18 are wound on a magnetically permeable, laminated core 38 made of a suitable material such as ferrite, laminated permealloy, or tape wound metglass. The tool 30 has a pair of orthogonal coils 16, 18 wound on a non-conductive core 38. In a preferred embodiment, a non-conductive, magnetically permeable core 38 is made of a suitable material such as ferrite, laminated permealloy, or tape-wound metglass. However, a non-conductive, non-magnetically permeable core 38 is within contemplation of this invention. The conductors of coils 16, 18 run axially along the tool 30. In a preferred embodiment, the angular density of the windings is sinusoidal to insure a two-dimensional dipolar field distribution. The coils 16, 18 are azimuthally offset by 90° to insure the dipolar fields of the coils 16, 18 are orthogonal in the formation and the mutual inductance of the coils 16, 18 is minimal. The coils 16, 18 are protected by a nonconductive, nonmagnetic, abrasion and impact resistant cover 36 made of a suitable material such as fiberglass, plastic, ceramic, or a composite of these materials.

Figure 3A:
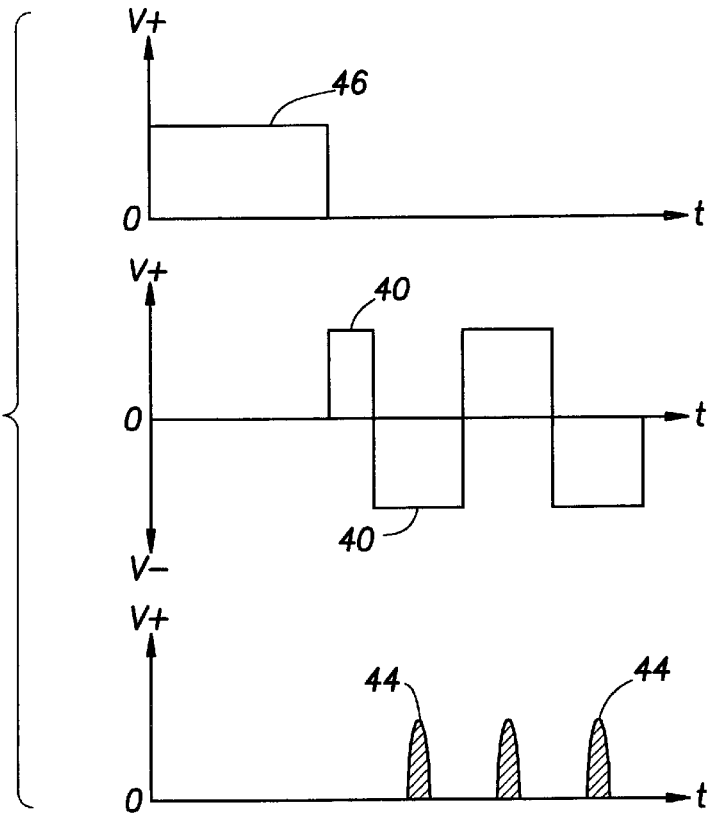
FIGS. 3a–3b show gradient echoes generated by simulating the apparatus of the subject invention.
Figure 3B:
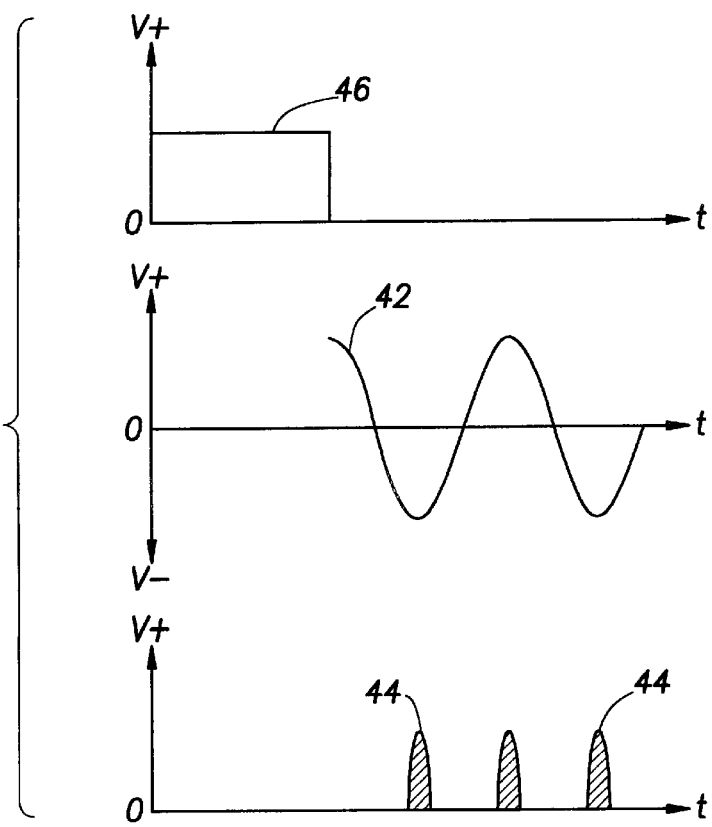

Referring to FIGS. 3a–3b, coil 16 is used to generate a static magnetic field that polarizes the spin magnetization. The spin magnetization is polarized by applying a direct current 46 to the coil 16 for a period of time approximately equal to or greater than the longitudinal relaxation time, $T_1$, of the formation thereby aligning the spins along the field $B_a$. The subject invention refocuses the magnetic moment of protons (spins) in the highly inhomogeneous field $B_a$ by reversing the direction of precession. Following polarization, coil 16 is turned off and coil 18, driven by either commutated direct current 40 or low frequency alternating current 42, is turned on. The spins initially aligned with $B_a$ start precessing in the plane that is perpendicular to $B_b$ at a precession frequency that is proportional to the strength of $B_b$. Reversing the direction of precession brings the spins to the phase at which they started precession, thus generating a gradient-echo 44. The free induction decay (FID) signal arising from the volume of investigation in the formation decays rapidly due to the inhomogeneous field. In a preferred embodiment, the gradient echoes are measured and the FID is not measured. The gradient-echoes 44 are detected using coil 16.

Figure 4:
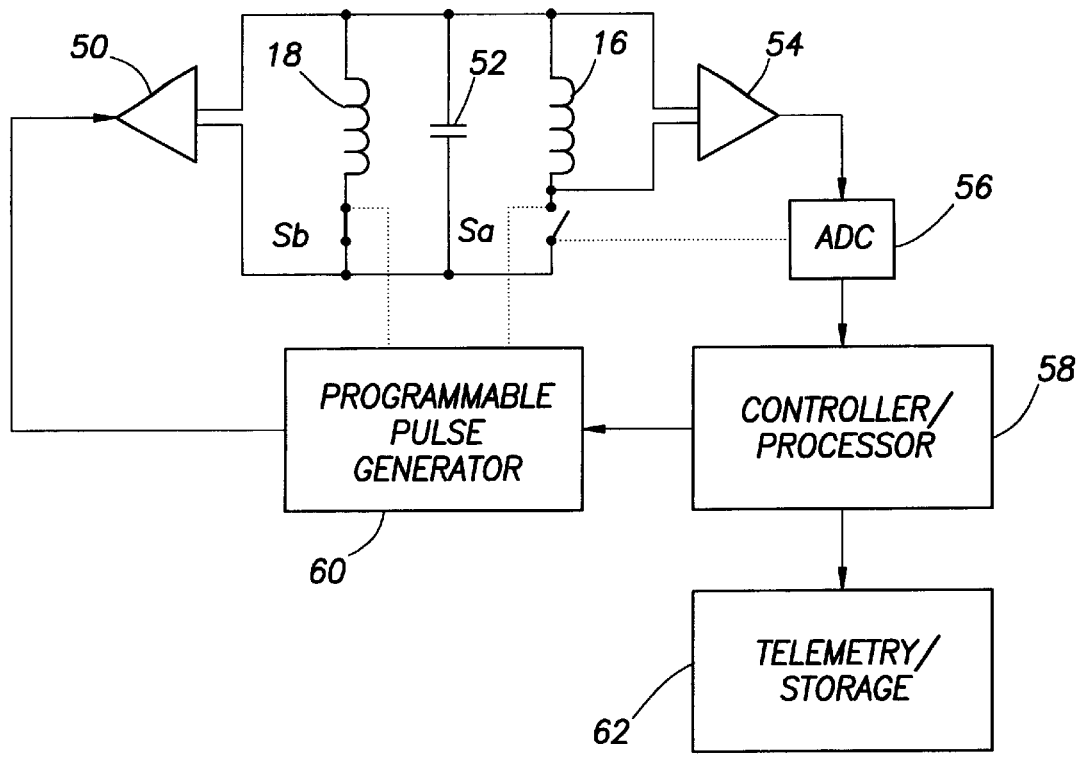
FIG. 4 depicts a block diagram of circuitry for the NMR logging tool.

Referring to FIG. 4, there is shown a block diagram of circuitry 22 for the logging tool 10, 30. The output of current source 50 is coupled to coils 16 and 18. Electronic switches $S_a$ and $S_b$ and capacitor 52 are coupled to coils 16 and 18. The output of coil 16 is coupled to a receiving section that includes an amplifier 54 and an analog-to-digital converter 56. The output of the analog-to-digital converter 56 is coupled to a downhole controller 58 with associated memory, timing, integer or floating point processor, and input/output circuitry. An output of the controller 58 is coupled to a programmable pulse generator 60 which, in turn, is coupled to the input of the current source 50. Telemetry/storage circuitry 62 is conventionally provided for communicating with the earth's surface.

The nuclear magnetic resonance circuitry in the subject invention can operate in three modes: polarization, switchover, and measurement. The polarization phase has a duration of approximately 0.01–8 seconds, based on the formation and the composition of the fluid in the rock pores. During the polarization phase, the nuclear spins in the formation are brought to their thermal equilibrium state in the magnetic field of coil 16. Current source 50 drives direct current through coil 16. Switch $S_a$ is closed and switch $S_b$ is open. These switches are controlled by the programmable pulse generator 60 and the controller 58. The amplifier 54, analog-to-digital converter 56, and coil 18 are inactive. At steady state, the capacitor 52 is charged up and current through the capacitor 52 ceases to flow. The entire current output of the current source 50 flows through coil 16. The amplifier 54 includes a DC blocking capacitor and a limiter to protect the amplifier from the large voltage on coil 16 during the polarization and switch-over phases.

Once the polarization phase ends, the switch-over phase begins with turning off the current source 50. Coil 16 and capacitor 52 form a resonator wherein the current in coil 16 is supplied by capacitor 52. When the current through coil 16 becomes zero, switch $S_a$ opens and switch $S_b$ closes thereby switching coil 16 with coil 18 in the resonator with minimal loss of energy. The current source 50 drives the resonator formed by coil 18 and capacitor 52 at its resonance frequency. The current source 50 can output either commutated direct current or low frequency alternating current at the resonant frequency. In either case, the current through coil 18 is alternating. The period of this alternating current determines the inter-echo time, $T_E$. The successive reversals of the magnetic field of coil 18 repeatedly refocus the phases of precessing spins thereby forming a sequence of equally spaced gradient-echoes. The period of this alternating current determines the inter-echo time, $T_E$. The period and the inter-echo time are preferably equal and approximately 1 msec.

Following switch-over, the amplified signal from amplifier 54 represents the voltage induced in coil 16 by precessing nuclear spins in the formation. The samples acquired by the analog-to-digital converter 56 can be written in the form $S_{0,n}, S_{1,n}, S_{2,n}, \ldots, S_{M-1,n}$ where M represents the total number of samples acquired by the analog-to-digital converter during the n-th gradient-echo. The samples $S_{0,n}, S_{1,n}, S_{2,n}, \ldots, S_{M-1,n}$ are equally spaced by a time interval of $\Delta t$ and are centered with respect to the n-th gradient echo. That is, $S_{0,n}$ and $S_{M-1,n}$ are equidistant in time from the center of the n-th gradient echo. The samples $S_{m,n}$ are Fourier-transformed with respect to the index m either by the controller 58 or by the processing system 14. The resulting frequency-domain samples $Y_{l,n}$ are:

$$Y_{l,n} = \text{Re}\left\{\sum_{m=0}^{M-1} S_{m,n} \exp(i2\pi . lm/M)\right\}; \quad l = 0, 1, \ldots, (M/2) - 1$$

The index l corresponds to the frequency $f_l=l/(M\Delta t)$ which in turn corresponds to the radial distance $r_l=\sqrt{cM\Delta t/l}$. The frequency is mapped to a radial position in the formation according to the relationship $f=c/r^2$, where r is the radial distance from the axis of the tool 10, 30 and the constant c is proportional to the product of the magnetic moment of coil 18 and the gyromagnetic ratio of protons, $\gamma$. For each l, that is for each radial position, $Y_{l,0}, Y_{l,1}, Y_{l,2}, \ldots, Y_{l,N-1}$ make up a sequence of echoes spaced by a time interval $T_E$. The echo sequence $Y_{l,0}, Y_{l,1}, Y_{l,2}, \ldots, Y_{l,N-1}$ is subject to spin—spin relaxation. The distribution of spin—spin relaxation times, $T_2$, at the radial position $r_l$ can be determined from the sequence $Y_{l,0}, Y_{l,1}, Y_{l,2}, \ldots, Y_{l,N-1}$ using the methods described in U.S. Pat. No. 5,363,041 issued to Abdurrahman Sezginer, which patent is incorporated herein by this reference. This images the NMR signal in the $(r, T_{2a})$ plane, where r is the radial distance from the axis of the tool and $T_{2a}$ is the apparent spin—spin relaxation time. The signal from the borehole fluid, which generally has a higher concentration of hydrogen nuclei compared to the formation, is discriminated from the formation signal by radial imaging; therefore, there is no need to dope the borehole fluid with a paramagnetic relaxing agent, such as manganese-EDTA.

The apparent spin—spin relaxation of a fluid is enhanced by molecular diffusion. In a fluid of diffusion coefficient D subject to a static field-gradient $G=\|\nabla B\|$, the apparent transverse relaxation time $T_{2a}$ is:

$$\frac{1}{T_{2a}} = \frac{1}{T_2} + \frac{D(GT_E\gamma)^2}{12}$$

where $T_2$ is the intrinsic spin—spin relaxation time of the fluid, $T_E$ is the time between spin-echoes, and $\gamma$ is the gyromagnetic ratio of protons. Measuring the apparent transverse relaxation time $T_{2a}$ for various values of G or $T_E$ provides an estimate of the diffusion coefficient D. The diffusion coefficient D is indicative of the fluid type. The diffusion coefficients of heavy hydrocarbons, water, and gaseous hydrocarbon are in ascending order and different by orders of magnitude. The matrix of a porous rock restricts molecular diffusion and reduces the effective diffusion coefficient below its bulk value. In a completely water saturated formation, the diffusion coefficient indicates the amount of restriction on molecular diffusion hence contains information about the pore geometry. Therefore, it is advantageous to measure the diffusion coefficient. The present invention provides a simultaneous measurement of the apparent transverse relaxation time $T_{2a}$ for multiple values of the field gradient $G=2c/r^3$ since each frequency, thus each radial position, corresponds to a particular value of the field-gradient G. Therefore, the effective diffusion coefficient of the formation fluid can be estimated from one train of gradient echoes.

Figure 7:
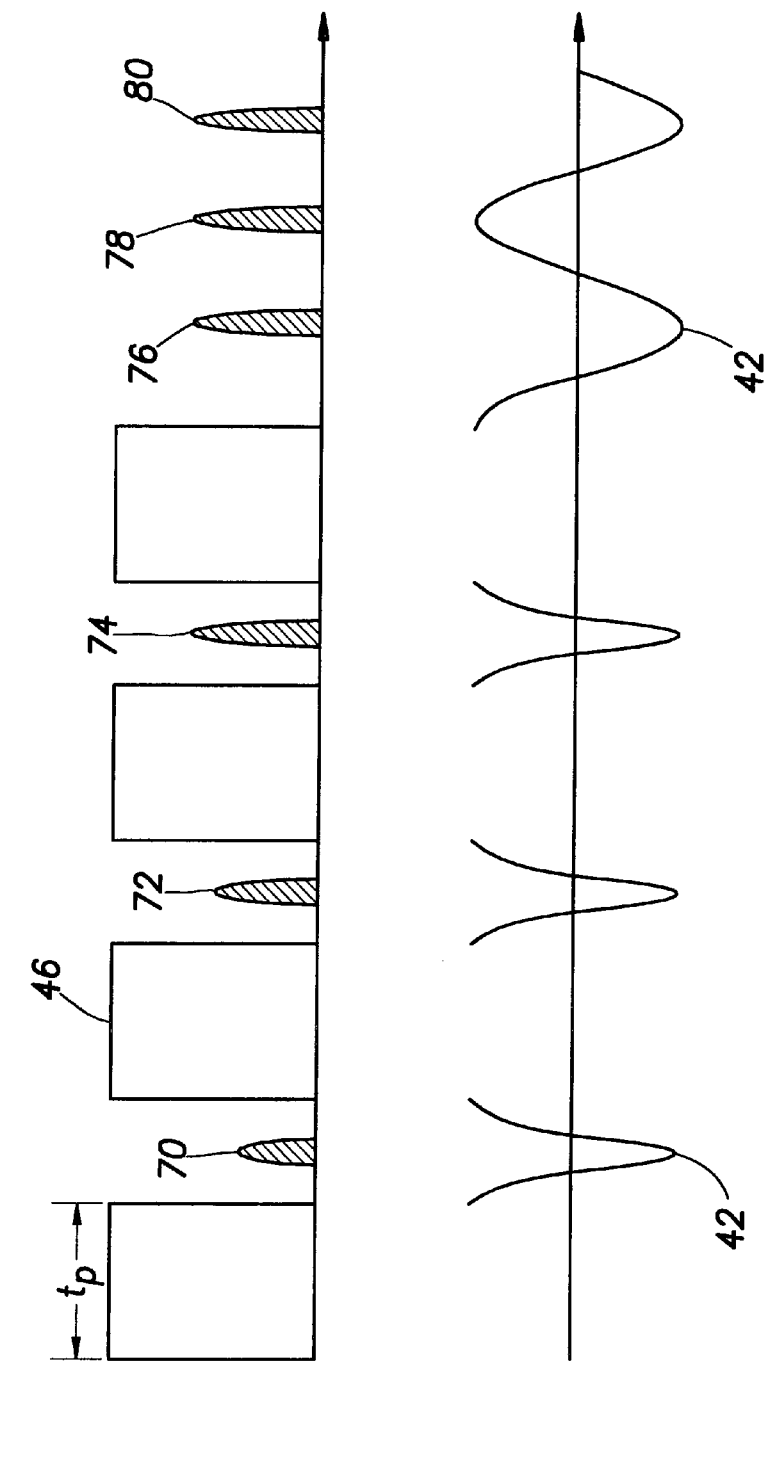

Another important parameter related to the property of pore fluid in earth formation is the longitudinal relaxation time, $T_1$. In addition to measuring $T_2$ as previously described herein, the subject invention can also measure the $T_1$ relaxation time. Referring to FIG. 7, coil 16 is used to generate a static magnetic field, $B_a$ in n-steps. For a length of time $t_p$, direct current 46 is applied to coil 16 during which time the spin magnetization is polarized according to the relationship $(1-e^{-tp/T1})$. Following $t_p$, coil 16 is turned off and a window is opened during which coil 18, driven either by commutated direct current or low frequency alternating current, is turned on. During the window period, a gradient-echo 70, 72, 74 is created by applying alternating current through coil 18. The gradient-echo 70, 72, 74 is detected using coil 16. At the end of the window period, the spin magnetization returns to the $B_a$ direction and continues to be polarized by the successive application of direct current 46. The characteristic time constant for the exponential buildup of this spin polarization is $T_1$ and the amplitude of the gradient-echo in the n-th step is proportional to $(1-e^{-ntp/T1})$. Following a period of time approximately equal to or greater than $T_1$, a gradient-echo train is stored in the memory and a second gradient-echo train 76, 78, 80 is created by applying alternating current through coil 18. The first gradient-echo train 70, 72, 74 and the second gradient-echo train 76, 78, 80 are inverse Laplace-transformed to extract the $T_1$ and $T_2$ relaxation times.

EXAMPLE

The method of this invention was tested in the laboratory using numerical simulations. In the simulation, the diameter of each coil 16 and 18 is 15.24 cm and the maximum magnetic field generated by the coils 16 and 18 is 58.7 G at a radial distance of $r_0$=7.62 cm. The precession frequency is 250 kHz at the surface of the tool and the field intensity decays as $1/r^2$.

Figure 5A:
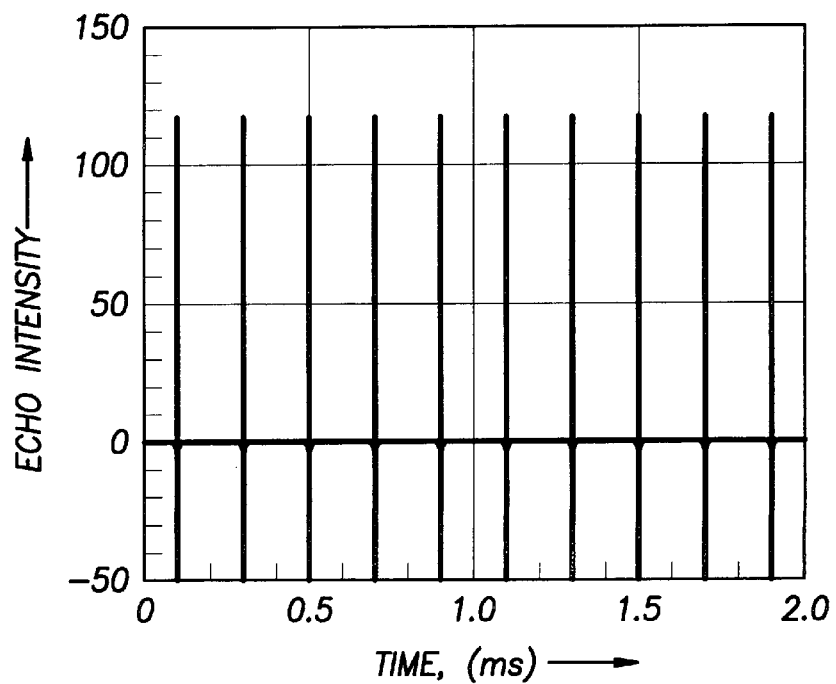
FIGS. 5a–5b illustrate two gradient echo trains generated by using square wave and cosine wave refocusing pulses to simulate commutated direct current and low frequency alternation current.
Figure 5B:
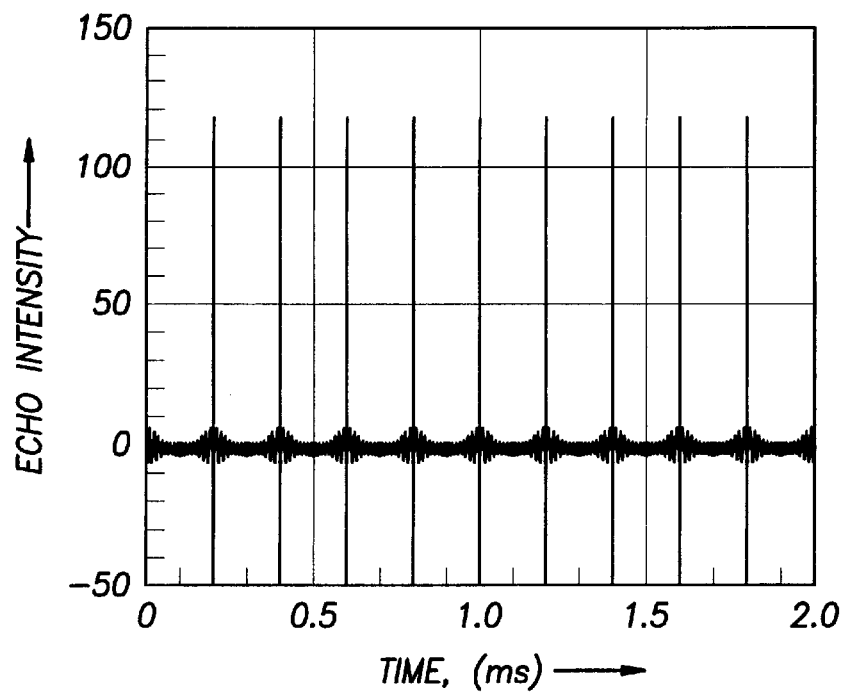

FIGS. 5a–5b show two gradient echo trains generated by using square wave and cosine wave refocusing pulses to simulate commutated direct current and low frequency alternation current, respectively. Assuming a negligible earth's magnetic field, the amplitude of the voltage induced in coil 16 due to spins at a cylindrical shell of radius r and thickness dr is:

$$dV=(\chi B_a)(\gamma B_b)(B_a/I_a)/\mu_0 2\pi rL dr,$$

where L is the length of the tool, $B_a/I_a$ is the sensitivity of the detector coil 16, $\chi$ is the nuclear magnetic susceptibility, and $\mu_0=4\pi\times10^{-7}$ Henry/m is the permeability of the vacuum. In the presence of magnetic fields $B_a=a/r^2$ and $B_b=b/r^2$, the voltage in the frequency domain is:

$$dV=-(\chi_f\pi La^2)/(r^2 I_a\mu_0)df, \text{ for } r>r_0, \text{ and}$$

$$dV=(\chi\pi La^2)/(bI_a\mu_0)fdf, \text{ for } f<\gamma b/r_0^2,$$

where a $\mu_0 N_a I_a$, b $\mu_0 N_b I_b$, and $N_a$, $N_b$, represent the number of turns of coil 16 and coil 18.

Figure 6:
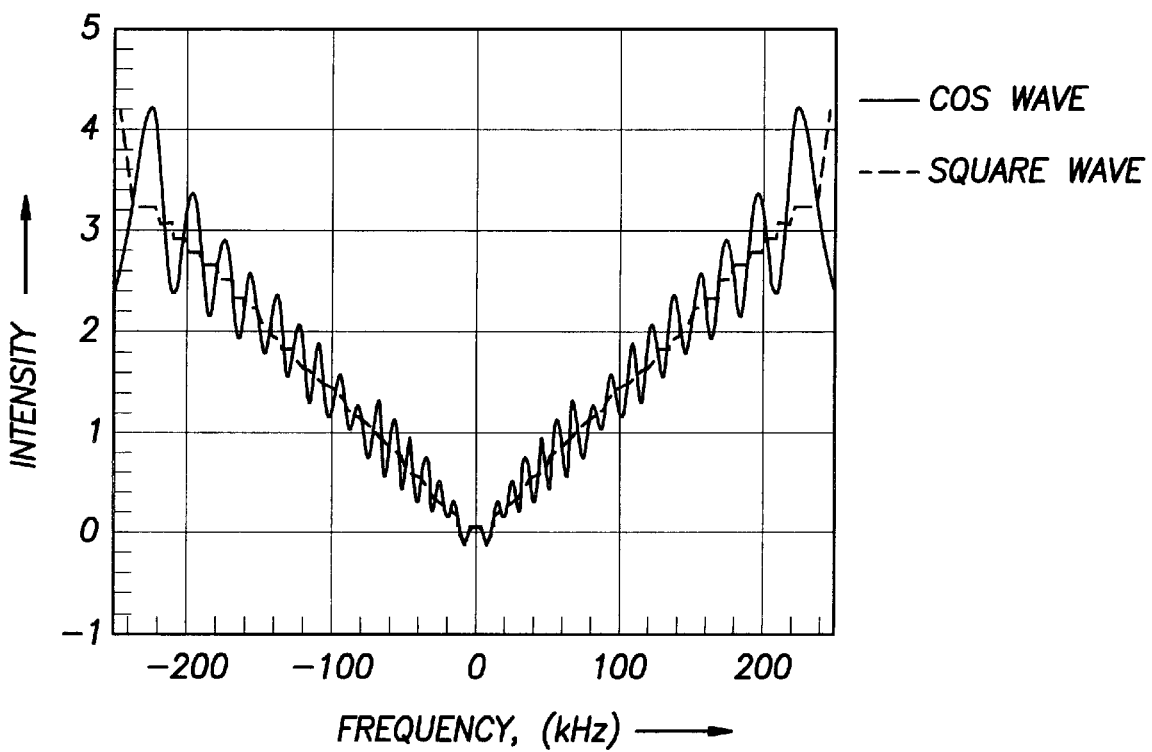
FIG. 6 illustrates the frequency spectra of the spin echoes obtained by using square-wave and cosine-wave refocusing pulses to simulate commutated direct current and low frequency alternating current; and, FIG. 7 illustrates two gradient echo trains used for simultaneously measuring $T_1$ and $T_2$ relaxation times.

FIG. 6 shows the frequency spectra of the spin echoes obtained by using square-wave and cosine-wave refocusing pulses to simulate commutated direct current and low frequency alternating current, respectively. The spectral intensity of the signal increases linearly with frequency, assuming a negligible earth's field. As the applied fields, $B_a$ and $B_b$, become comparable to $B_e$, the signal decreases faster because the pre-polarized magnetization becomes substantially parallel to the axis of precession. For the numerical simulation, the depth of investigation where the magnitude of magnetic fields $B_a$, $B_b$ approach the magnitude of the earth's field, $B_E$, is determined by $r_{max}=(b/B_e)^{1/2}$ which is approximately 81.28 cm.

The foregoing description of the preferred and alternate embodiments of the present invention have been presented for purposes of illustration and description. It is not intended to be exhaustive or limit the invention to the precise form disclosed. Obviously, many modifications and variations will be apparent to those skilled in the art. For example, a permanent magnet may generate the static magnetic field, $B_a$, or the magnetic field, $B_b$. Further, the train of gradient-echoes may be used to determine the porosity of the formation. The embodiments were chosen and described in order to best explain the principles of the invention and its practical application thereby enabling others skilled in the art to understand the invention for various embodiments and with various modifications as are suited to the particular use contemplated. It is intended that the scope of the invention be defined by the accompanying claims and their equivalents.

What I claim is:

1. An apparatus for measuring a nuclear magnetic resonance property of earth formations surrounding a borehole, without the application of RF pulses, comprising:
   a) means for applying a static magnetic field, Ba, in a volume of the formation which polarizes the nuclei of hydrogenous connate fluids within the formation;
   b) means for applying a static magnetic field, Bb, in the volume of the formation such that the static magnetic fields Ba, and Bb are substantially orthogonal in the volume of the formation and a change in polarity of the magnetic field Bb reverses the direction of precession thereby generating a gradient echo; and,
   c) means for detecting a signal induced in the formation after the nuclei begin to precess in the plane perpendicular to static magnetic field Bb wherein the precession frequency is proportional to the strength of static magnetic field Bb.

2. The apparatus of claim 1 wherein the means for applying a static magnetic field, Ba, comprises:
   a) a first coil; and,
   b) a means for supplying direct current to the first coil.

3. The apparatus of claim 2 wherein the means for applying a static magnetic field, Bb, comprises:
   a) a second coil; and,
   b) a means for supplying an alternating current signal to the second coil.

4. The apparatus of claim 3, further comprising a switching means for selectively activating the first or second coil.

5. The apparatus of claim 4, further comprising a resonator means for sustaining current in the first or second coil during selective activation of the other coil.

6. The apparatus of claim 5 wherein the resonator means comprises a capacitor operatively connected to the first coil.

7. The apparatus of claim 5 wherein the resonator means comprises a capacitor operatively connected to the second coil.

8. The apparatus of claim 4, further comprising means for controlling the switching means such that the first coil is selected and activated for a time period, following the time period, the first coil is deactivated, and the second coil is selected and activated after the current ceases to flow through the first coil.

9. The apparatus of claim 8 wherein the static magnetic field, Ba, is applied for at least a time approximately equal to the longitudinal relaxation time of the formation.

10. The apparatus of claim 1 wherein the magnitude of the applied static magnetic fields Ba and Bb are substantially greater than the earth's magnetic field, $B_E$.

11. The apparatus of claim 3 wherein the first and second coils are wound on a magnetic body.

12. The apparatus of claim 11 wherein the coils are wound longitudinally around the body and azimuthally offset by 90°.

13. The apparatus of claim 11 wherein the first coil is wound longitudinally around the body and the second coil is wound circumferentially around the body.

14. The apparatus of claim 1 wherein the means for applying the static magnetic field, Ba, comprises a permanent magnet.

15. The apparatus of claim 3 wherein the first and second coils are wound on a non-conductive body.

16. The apparatus of claim 3 wherein the first and second coils are wound on a conductive body.

17. The apparatus of claim 3 wherein the first and second coils are wound on a non-magnetic body.

18. An apparatus for measuring a nuclear magnetic resonance property of earth formations surrounding a borehole, without the application of RF pulses, comprising:
   a) means for drilling a borehole in the formation;
   b) a measuring means, connected to the drilling means, for making nuclear magnetic resonance measurements while the borehole is being drilled, without the application of RF pulses, the measuring means comprising:
      I) means for applying a static magnetic field, Ba, in a volume of the formation which polarizes the nuclei of hydrogenous connate fluids within the formation;
      II) means for applying a static magnetic field, Bb, in the volume of the formation such that the static magnetic fields Ba and Bb are substantially orthogonal in the volume of the formation and a change in polarity of the magnetic field Bb reverses the direction of precession thereby generating a gradient echo; and,
      III) means for detecting a signal induced in the formation after the nuclei begin to precess in the plane perpendicular to Bb wherein the precession frequency is proportional to the strength of Bb.

19. The apparatus of claim 18 wherein the means for applying a static magnetic field, $B_a$, comprises:
   a) a first coil; and,
   b) a means for supplying direct current to the first coil.

20. The apparatus of claim 19 wherein the means for applying a magnetic field, $B_b$, comprises:
   a) a second coil; and,
   b) a means for supplying an alternating current signal to the second coil.

21. The apparatus of claim 20, further comprising a switching means for selectively activating the first or second coil.

22. The apparatus of claim 21, further comprising a resonator means for sustaining current in the first or second coil during selective activation of the other coil.

23. The apparatus of claim 22 wherein the resonator means comprises a capacitor operatively connected to the first coil.

24. The apparatus of claim 22 wherein the resonator means comprises a capacitor operatively connected to the second coil.

25. The apparatus of claim 21, further comprising means for controlling the switching means such that the first coil is selected and activated for a time period, following the time period, the first coil is deactivated, and the second coil is selected and activated after the current ceases to flow through the first coil.

26. The apparatus of claim 25 wherein the static magnetic field, $B_a$, is applied for at least a time approximately equal to the longitudinal relaxation time of the formation.

27. The apparatus of claim 18 wherein the magnitude of the magnetic field $B_a$ and $B_b$ is substantially greater than the earth's magnetic field, $B_E$.

28. The apparatus of claim 20 wherein the first and second coils are wound on a magnetic body.

29. The apparatus of claim 28 wherein the coils are wound longitudinally around the body and azimuthally offset by 90°.

30. The apparatus of claim 28 wherein the first coil is wound longitudinally around the body and the second coil is wound circumferentially around the body.

31. The apparatus of claim 18 wherein the means for applying the static magnetic field, $B_a$, comprises a permanent magnet.

32. The apparatus of claim 18 wherein the means for applying the magnetic field, $B_b$, comprises a permanent magnet.

33. The apparatus of claim 20 wherein the first and second coils are wound on a non-conductive body.

34. The apparatus of claim 20 wherein the first and second coils are wound on a conductive body.

35. The apparatus of claim 20 wherein the first and second coils are wound on a non-magnetic body.

36. A method for measuring a nuclear magnetic resonance property of earth formations surrounding a borehole, comprising the steps:
   a) applying a static magnetic field, Ba, in a volume of the formation which polarizes the nuclei of hydrogenous connate fluids within the formation;
   b) applying a static magnetic field, Bb, in the volume of the formation such that the static magnetic fields Ba and Bb are substantially orthogonal in the volume of the formation and a change in the polarity of the magnetic field Bb reverses the direction of precession thereby generating a gradient echo; and,
   c) detecting a signal induced in the formation after the nuclei begin to precess in the plane perpendicular to Bb wherein the precession frequency is proportional to the strength of static magnetic field, Bb.

37. The method of claim 36 further comprising the steps of providing at least two coils and selectively activating one coil.

38. The method of claim 37 further comprising the step of sustaining current in the other coil during selective activation of the one coil.

39. The method of claim 37 further comprising the steps of selecting and activating the one coil for a time period, deactivating the one coil following the time period, and selecting and activating the other coil after current ceases to flow through the one coil.

40. A method for measuring a nuclear magnetic resonance property of earth formations surrounding a borehole, without the application of RF pulses, comprising the steps:
   a) drilling a borehole in the formation;
   b) measuring the nuclear magnetic resonance response while the borehole is being drilled, without the application of RF pulses, comprising the steps:
      I) applying a static magnetic field, Ba, in a volume of the formation which polarizes the nuclei of hydrogenous connate fluids within the formation;
      II) applying a static magnetic field, Bb, in the volume of the formation such that the static magnetic fields Ba and Bb are substantially orthogonal in the volume of the formation and a change in the polarity of the magnetic field Bb reverses the direction of precession thereby generating a gradient echo; and,
      III) detecting a signal induced in the formation after the nuclei begin to precess in the plane perpendicular to Bb wherein the precession frequency is proportional to the strength of Bb.

41. The method of claim 40 wherein the static magnetic field is applied by a first coil and further comprising the step of supplying direct current to the first coil.

42. The method of claim 41 wherein the magnetic field, $B_b$, is applied by a second coil and further comprising the step of supplying an alternating current signal to the second coil.

43. The method of claim 42 further comprising the step of selectively activating the first or second coil.

44. The method of claim 43 further comprising the step of sustaining current in the first or second coil during selective activation of the other coil.

45. The method of claim 43 further comprising the steps of selecting and activating the first coil for a time period, deactivating the first coil following the time period, and selecting and activating the second coil after current ceases to flow through the first coil.

46. A method for nuclear magnetic resonance imaging of an earth formation surrounding a fluid-filled borehole, without the application of RF pulses, comprising the steps of:
  a) applying a static magnetic field, Ba, in a volume of the formation which polarizes the nuclei of hydrogenous connate fluids within the formation;
  b) applying a static magnetic field, Bb, in the volume of the formation such that the static magnetic fields Ba and Bb are substantially orthogonal in the volume of the formation and a chance in the polarity of the magnetic field Bb reverses the direction of precession thereby generating a gradient echo signal;
  c) detecting the signal;
  d) transforming the signal into the frequency-domain; and,
  e) mapping the signal frequency to a radial position in the volume of the formation to produce an image of the formation.

47. The method of claim 46 wherein the image is produced for a range in the volume of the formation extending radially from the borehole axis to a position in the formation where the magnitude of the magnetic field, $B_b$, approaches the magnitude of the earth's field, $B_E$.

48. The method of claim 46 wherein the signal from the borehole fluid and the formation are distinguished by the respective radial positions.

49. The method of claim 46 further comprising the step of estimating the coefficient of molecular diffusion in the pore-fluid of the earth formation based upon the sequence of gradient echoes.

50. The method of claim 46 wherein the nuclear magnetic resonance imaging occurs while drilling the borehole.

51. A method of obtaining nuclear magnetic resonance information from an earth formation traversed by a borehole, without the application of RF pulses, comprising the steps of:
  a) applying a first static magnetic field in a volume of the formation;
  b) applying a second static magnetic field in the volume of the earth formation;
  c) generating a gradient echo signal; and,
  d) detecting the gradient echo signal.

52. The method of claim 51 wherein the gradient echo signal is generated by changing the polarity of the second magnetic field.

53. The method of claim 51, further comprising the step of transforming the gradient echo signal into the frequency-domain and mapping the signal frequency to a radial position in the volume of the formation to produce an image of the formation.

54. The method of claim 51 wherein the nuclear magnetic resonance information is obtained while drilling the borehole.

55. An apparatus for obtaining nuclear magnetic resonance information from an earth formation traversed by a borehole, without the application of RF pulses, comprising:
  a) means for applying a first static magnetic field to a volume of the formation;
  b) means for applying a second static magnetic field to the volume of the formation;
  c) means for generating a gradient echo; and,
  d) means for detecting the gradient echo.

56. The apparatus of claim 55 further comprising means for changing the polarity of the second magnetic field.

57. The apparatus of claim 55 further comprising means for transforming the gradient echo signal into the frequency-domain and means for mapping the signal frequency to a radial position in the volume of the formation to produce an image of the formation.

58. The apparatus of claim 55 wherein the nuclear magnetic resonance information is obtained while drilling the borehole.

59. A method for measuring the longitudinal relaxation time and spin—spin relaxation time of an earth formation, without the application of RF pulses, comprising the steps of
  a) generating a first gradient echo train during a magnetization preparation period;
  b) following the magnetization preparation period, generating a second gradient echo train; and,
  c) extracting the longitudinal relaxation time from the first gradient echo train and extracting the spin—spin relaxation time of the formation from the second gradient echo train.

60. The method of claim 59 wherein step (a) further comprises the steps of
  I) applying a first static magnetic field for a time period less than the magnetization preparation period;
  II) deactivating the first magnetic field;
  III) applying a second static magnetic field;
  IV) changing the polarity of the second magnetic field thereby generating a gradient echo;
  V) deactivating the second static magnetic field; and,
  VI) repeating steps (i)–(v) to generate the first gradient echo train.

61. The method of claim 59 wherein step (b) further comprises the steps of
  i) applying a second static magnetic field; and,
  ii) successively changing the polarity of the second magnetic field thereby forming a sequence of equally spaced gradient echoes.

62. The method of claim 59 wherein the longitudinal and spin—spin relaxation times are obtained while drilling a borehole through the earth formation.

63. The method of claim 46 further comprising the step of estimating the porosity of the earth formation based upon the sequence of gradient echoes.

* * * * *